(12) United States Patent
Lobner et al.

(10) Patent No.: US 10,881,327 B2
(45) Date of Patent: Jan. 5, 2021

(54) ACTIVITY RECOGNITION USING ACCELEROMETER DATA

(71) Applicant: 3M INNOVATIVE PROPERTIES COMPANY, St. Paul, MN (US)

(72) Inventors: Eric C. Lobner, Woodbury, MN (US); James W. Howard, Circle Pines, MN (US); Richard J. Moore, Maplewood, MN (US); Jennifer F. Schumacher, Woodbury, MN (US); Brian J. Stankiewicz, Mahtomedi, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 473 days.

(21) Appl. No.: 15/117,943

(22) PCT Filed: Feb. 12, 2015

(86) PCT No.: PCT/US2015/015534
§ 371 (c)(1),
(2) Date: Aug. 10, 2016

(87) PCT Pub. No.: WO2015/123373
PCT Pub. Date: Aug. 20, 2015

(65) Prior Publication Data
US 2016/0354014 A1 Dec. 8, 2016

Related U.S. Application Data

(60) Provisional application No. 61/939,832, filed on Feb. 14, 2014.

(51) Int. Cl.
*A61B 5/11* (2006.01)
*A61B 5/00* (2006.01)

(52) U.S. Cl.
CPC .......... *A61B 5/1123* (2013.01); *A61B 5/0004* (2013.01); *A61B 5/1118* (2013.01);
(Continued)

(58) Field of Classification Search
None
See application file for complete search history.

(56) References Cited

U.S. PATENT DOCUMENTS 5,137,345 A  8/1992 Waldorf
5,295,491 A  3/1994 Gevins
(Continued)

FOREIGN PATENT DOCUMENTS

EP  2330554  6/2011
GB  2447647  9/2008
(Continued)

OTHER PUBLICATIONS

US 7,877,241 B2, 01/2011, Elmer (withdrawn)
(Continued)

*Primary Examiner* — David J. McCrosky
(74) *Attorney, Agent, or Firm* — Steven A. Bern; Christopher D. Karlen

(57) ABSTRACT

A device for recognizing activity of an object. The device has a housing configured to be attached to the object and a processing unit disposed in the housing has a processor and a movement sensor. The movement sensor measures a signal related to the movement of the object during a time window. The processor assigns at least one preliminary activity label to the time window based on at least one numerical descriptor computed from the signal. The processor then determines whether to perform additional analysis dependent upon at least the preliminary activity label. The processor then assigns a final activity label to the time window.

20 Claims, 4 Drawing Sheets

(52) U.S. Cl.
CPC .......... *A61B 5/6828* (2013.01); *A61B 5/7264* (2013.01); *A61B 5/7282* (2013.01); *A61B 2562/0219* (2013.01)

(56) References Cited

U.S. PATENT DOCUMENTS

| | | | |
|---|---|---|---|
| 5,325,862 A | 7/1994 | Lewis | |
| 5,421,344 A | 6/1995 | Popp | |
| 5,485,402 A | 1/1996 | Smith | |
| 6,032,530 A | 3/2000 | Hock | |
| 6,511,443 B2 | 1/2003 | Cuce | |
| 7,421,369 B2 | 9/2008 | Clarkson | |
| 7,451,056 B2 | 11/2008 | Flentov | |
| 7,653,508 B1 | 1/2010 | Kahn | |
| 7,750,815 B2 | 7/2010 | Burris | |
| 7,818,131 B2 | 10/2010 | Mott | |
| 8,036,851 B2 | 10/2011 | Vock | |
| 8,078,334 B2 | 12/2011 | Goodrich | |
| 8,187,209 B1 | 5/2012 | Giuffrida | |
| 8,206,325 B1 | 6/2012 | Najafi | |
| 8,226,574 B2 | 7/2012 | Whillock | |
| 9,795,335 B2* | 10/2017 | Merfeld | A61B 5/16 |
| 9,808,206 B1* | 11/2017 | Zhao | A61B 5/7282 |
| 2002/0045835 A1* | 4/2002 | Masakov | A61B 5/0205 |
| | | | 600/481 |
| 2005/0027216 A1 | 2/2005 | Guillemaud | |
| 2007/0124135 A1 | 5/2007 | Schultz | |
| 2007/0208530 A1 | 9/2007 | Vock | |
| 2007/0225614 A1 | 9/2007 | Naghavi | |
| 2008/0162088 A1* | 7/2008 | DeVaul | A61B 5/0024 |
| | | | 702/190 |
| 2009/0024005 A1* | 1/2009 | Lewicke | A61B 5/1116 |
| | | | 600/301 |
| 2009/0069722 A1 | 3/2009 | Flaction | |
| 2009/0240463 A1 | 9/2009 | Lee | |
| 2009/0316983 A1 | 12/2009 | Han | |
| 2010/0161706 A1 | 6/2010 | Kim | |
| 2010/0191155 A1 | 7/2010 | Kim | |
| 2010/0238033 A1* | 9/2010 | Blumel | A61B 5/1112 |
| | | | 340/573.4 |
| 2011/0029465 A1 | 2/2011 | Ito | |
| 2011/0077919 A1 | 3/2011 | Lee | |
| 2011/0137836 A1* | 6/2011 | Kuriyama | A61B 5/1118 |
| | | | 706/12 |
| 2011/0213276 A1 | 9/2011 | Sarussi | |
| 2012/0004883 A1 | 1/2012 | Vock | |
| 2014/0365163 A1* | 12/2014 | Jallon | A61B 5/1116 |
| | | | 702/141 |

FOREIGN PATENT DOCUMENTS

| | | |
|---|---|---|
| IN | 2389-CHE-2009 | 4/2011 |
| JP | H04-250141 | 9/1992 |
| JP | 2009-023545 | 2/2009 |
| RU | 2146494 | 3/2000 |
| WO | WO 2009-090584 | 7/2009 |
| WO | WO 2010/083562 | 7/2010 |
| WO | WO 2013-142379 | 9/2013 |

OTHER PUBLICATIONS

Three Office Actions issued for Australian patent application No. 2015-217160.*

"Assessing the Feasibility of Vehicle-Based Sensors to Detect Alcohol Impairment" National Highway Traffic Safety Administration Report No. DOT HS 811358, Aug. 2010, pp. 98.

Dai, "Mobile Phone Based Drunk Driving Detection," 4th International Conference on Pervasive Computing Technologies for Healthcare, Mar. 2010, 8 pgs.

"Intelligent Fingerprinting" [retrieved from internet on Sep. 28, 2016], URL <http://www.intelligentfingerprinting.com/>, 1 pg.

Labcorp, "Drugs of Abuse Reference Guide" Laboratory Corporation of America, 2007, 1 pg.

Rassnick, "Responding to Acoustic Startle During Chronic Ethanol Intoxication and Withdrawal" Psychopharmacology, Mar. 1992, vol. 106, No. 3, pp. 351-358.

"Remote Monitoring System for Detecting Cocaine Ingestion / Intoxication (R01)," National Institute of Health, Posted on May 23, 2011, [retrieved from internet on Sep. 28, 2016], URL <http://grants.nih.gov/grants/guide/rfa-files/RFA-DA-12-007.html>, 14pgs.

"Simmersion, Training People for Important Conversations," [retrieved from internet on Sep. 28, 2016], URL <http://www.simmersion.com/>, 5 pgs.

International Search Report for PCT International Application No. PCT/US2015/015534, dated May 8, 2015, 3pgs.

* cited by examiner

ACTIVITY RECOGNITION USING ACCELEROMETER DATA

CROSS REFERENCE TO RELATED APPLICATIONS

This application is a national stage filing under 35 U.S.C. 371 of PCT/US2015/015534, filed Feb. 12, 2015, which claims the benefit of Provisional Application No. 61/939,832, filed Feb. 14, 2014, the disclosure of which is incorporated by reference in its/their entirety herein.

TECHNICAL FIELD

The present invention relates to the field of recognizing or classifying movement. More specifically, it relates to the field of recognizing an activity of a body, person or object using data from a movement sensor in an activity recognition device attached to the individual.

BACKGROUND

Human, body or object activity recognition or classification has been attempted with a variety of technologies ranging from cameras, microphones, inertial sensors, and combinations of these devices utilizing various algorithms. Of these solutions, inertial sensors, tilt sensors and other motion sensors can provide a relatively simple way of gathering data related to a human's, body's or object's motion. These sensors are particularly attractive because they do not require use of a static device observing movement of an individual and because they can be conveniently carried or attached to an individual.

Even in light of the general advantages provided by inertial, tilt and other sensors, recognizing and classifying movement based on data from inertial or other motion sensors still presents a variety of challenges. For example, some inertial sensors have no notion of a frame of reference and any measurements made by such inertial sensors are also relative to the physical disposition of the sensor performing the measurement. Additionally, inertial sensors often have arbitrary offset and scale factors which affect the usability of output from the sensor.

An improved way to use movement or inertial sensors in recognizing and classifying movement would be welcomed.

SUMMARY

The present invention provides an improved device and methods for recognizing activity of an object, body, or person. Objects include both animate and inanimate forms. A body includes animate creatures, such as animals or humans, and a person includes only humans. Using data from a movement sensor, it provides an activity recognition solution with the ability to process data in a resource-constrained environment. Further, the present invention increases accuracy in activity recognition by providing additional analysis based on a variety of factors. The additional analysis can be run on a second or external processor and the results of such analysis can be transmitted to the activity recognition device. Further, in contexts where location monitoring systems, such as those relying on Global Positioning Systems (GPS), are used, the present invention can provide a secondary monitoring method for classifying activities that can verify or trigger alerts or alarms based on the person's recognized activity and/or spatial location.

In one instance, the present invention relates to a device for recognizing activity of an object. The device comprises a housing configured to be attached to the object and a processing unit disposed in the housing comprising a processor and a movement sensor. The movement sensor measures a signal related to movement of the object during a time window. The processor assigns at least one preliminary activity label to the time window based on at least one numerical descriptor computed from the signal. The processor then determines whether to perform additional analysis dependent upon at least the preliminary activity label. The processor then assigns a final activity label to the time window.

In another instance, the present invention includes a device for recognizing activity of an object. The device comprises a housing configured to be attached to the object and a processing unit disposed in the housing comprising a processor and a movement sensor. The movement sensor measures a signal related to movement of the object during a time window. The processor assigns at least one preliminary activity label and confidence indicator to the time window based on at least one numerical descriptor computed from the signal. The processor then determines whether to perform additional analysis dependent upon at least the confidence indicator; and the processor assigns a final activity label to the time window.

In another instance, the present invention includes a method of recognizing activity of an object. The method comprises measuring, with a movement sensor attached to the object, a signal related to movement of the object during a time window. The method further comprises assigning, with a processor, at least one preliminary activity label to the time window based on at least one numerical descriptor computed from the signal. The method then includes determining whether to perform additional analysis dependent upon at least the preliminary activity label; and assigning a final activity label to the time window.

In yet another instance, the present invention includes a method of recognizing activity of an object. The method comprises measuring, with a movement sensor attached to the object, a signal related to movement of the object during a time window. The method further includes assigning, with a processor, at least one preliminary activity label to the time window based on at least one numerical descriptor computed from the signal. The method then includes determining whether to perform additional analysis dependent upon at least the preliminary activity label, and assigning a final activity label to the time window.

In another instance, the present invention includes a device for recognizing activity of an object, the device comprising a housing configured to be attached to the object and a processing unit disposed in the housing comprising a communication unit and a movement sensor. The movement sensor measures a signal related to movement of the object during a time window, and the communication unit communicates the signal to an exterior processor. The exterior processor assigns at least one preliminary activity label to the time window based on at least one numerical descriptor computed from the measured signal. The exterior processor determines whether to perform additional analysis dependent upon at least the preliminary activity label; and the exterior processor assigns a final activity label to the time window.

In another configuration, the present invention includes a device for recognizing activity of an object, the device comprising a housing configured to be attached to the object and a processing unit disposed in the housing comprising a communication unit and a movement sensor. The movement sensor measures a signal related to movement of the object during a time window and the communication unit communicates the signal to an exterior processor. The exterior processor assigns at least one preliminary activity label and confidence indicator to the time window based on at least one numerical descriptor computed from the measured signal. The exterior processor determines whether to perform additional analysis dependent upon at least the confidence indicator, and the exterior processor assigns a final activity label to the time window.

BRIEF DESCRIPTION OF DRAWINGS

The following figures provide illustrations of the present invention. They are intended to further describe and clarify the invention, but not to limit scope of the invention.

Like numbers are generally used to refer to like components. The drawings are not to scale and are for illustrative purposes only.

DETAILED DESCRIPTION

Figure 1:
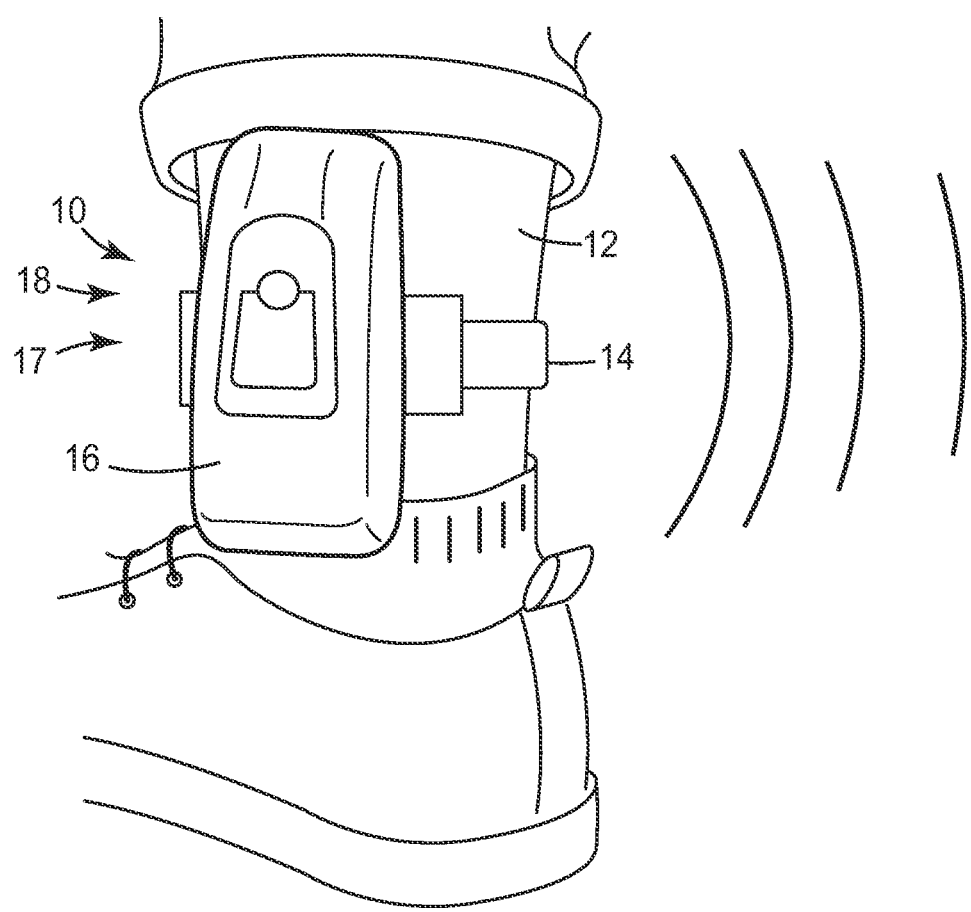
FIG. 1 is an example of an activity recognition device attached to a person.

FIG. 1 is an example of an activity recognition device 10 attached to a person's ankle 12. Activity recognition device 10 is attached to person's ankle 12 or other limb with strap 14. The housing 16 for activity recognition device 10 includes or contains a variety of components such as a processing unit 17, including both a processor and movement sensor, and a communication unit 18 for communicating wirelessly with an external device. A processor in processing unit may also include memory for storing data received from the movement sensor, preliminary and final activity labels, and other information. A movement sensor may include at least one of a variety of sensors, including an accelerometer, gyroscope, piezoelectric vibration sensor, geographical positioning sensor and a magnetic switch. A movement sensor can be configured to measure a signal related to movement of the person during a time window. A processor may compute at least one numerical descriptor from the measured signal and assign at least one preliminary activity label to the time window based on the numerical descriptor. The processor may then determine whether to perform additional analysis dependent upon at least the preliminary activity label; and then the processor assigns a final activity label to the time window.

In another configuration, the processor may assign at least one preliminary activity label and confidence indicator to the time window based on at least one numerical descriptor computed from the measured signal. The processor may then determine whether to perform additional analysis dependent upon at least the confidence indicator and the processor then assigns a final activity label to the time window.

Activity recognition device 10 may also include other components such as a location unit that enables the device to receive satellite signals and determine location using, for example, GPS or the Global Navigation Satellite System (GLONASS). A location unit may use other location technologies such as triangulation using local WiFi signals or other known location technologies to estimate location of the activity recognition device 10, and thereby the location of the person wearing the device.

Figure 2:
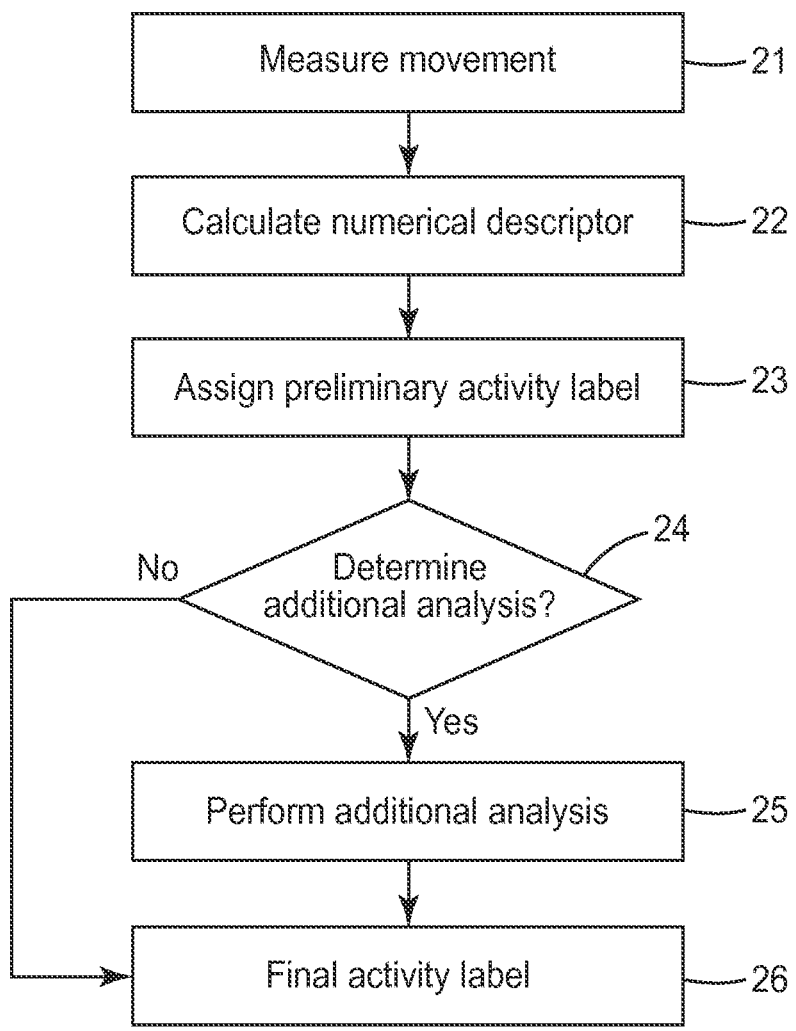
FIG. 2 is a flow chart representing a method of detecting an activity performed by a person.

FIG. 2 is a flow chart representing a method of detecting an activity performed by a person by an activity recognition device. In step 21, the movement sensor measures the movement of the person to which the activity recognition device is attached. An activity recognition device could be attached in a variety of ways, such as by being secured by a strap to the person's ankle or wrist. The activity recognition device could also be placed in the individual's pocket, clipped to a belt, or connected to their body by a variety of arrangements. When the activity recognition device measures the movement of the person, the data associated with that measurement may be in a variety of forms or units, and will typically depend on the type of movement sensor included in the activity recognition device. As an example, if an accelerometer is used as a sensor, measurement would be quantified in meters per second per second ($m/s^2$) or g-force (g). A gyroscope may quantify data as torque measured in Newton meters (N·m). The data collected to measure movement can be collected at any desired sample rate. In some instances the sample rate may be in the range of one (1) Hz to twenty (20) Hz. Sampling occurs over a series of time windows such that there are multiple samples taken per time window. An exemplary time window may be in the range of 1 to 10 seconds, more specifically, in the range of 4 to 8 seconds, and for example, an exemplary time window may last for 6 seconds.

In step 22, the activity recognition device calculates at least one numerical descriptor associated with the data sampled over one or more time windows. The numerical descriptor is a number computed based on the data sampled from a signal measured by the movement sensor. The numerical descriptor may be based on a single measured signal or on multiple measured signals. For example, when the movement sensor detects inertial movement along three axes, the numerical descriptor may be calculated based on the data associated with each of the three axes. The numerical descriptor may be determined for each data point related to the measured signal(s) or may be based on a lower sampling rate than the data from the measured signals. In some instances, two or more numerical descriptors may be associated with each time window.

In step 23, the activity recognition device assigns a preliminary activity label to each time window. In some instances, the processor may assign more than one preliminary activity label to a given time window. The preliminary activity label may be based on the use of the measured signal or the numerical descriptor. For example, the activity recognition device processor may use a decision tree to determine a preliminary activity for a given time window. Depending on the value of the data from the measured signal and the numerical descriptor, the confidence indicator associated with the assignment of a given preliminary activity label to a given time window may vary. A confidence indicator may be a scalar number, a probability, or some other method of designating confidence of the accuracy of the given preliminary activity label. In instances where more than one preliminary activity labels is assigned to a time window, each preliminary activity label may also have a confidence indicator associated with it.

Examples of preliminary activity labels include: walking, driving, sleeping, sitting, running, eating, and bicycling. Other preliminary activity labels may also be assigned depending on the importance of identifying various activities.

In step 24, the activity recognition device determines whether additional analysis will be performed prior to assigning a final activity label in step 26. The determination of whether to perform may depend on a variety of factors. In one configuration, it may be dependent on the confidence indicator associated with the particular time window. For example, if confidence indicator is indicated as a probability, a confidence indicator below a predefined threshold probability may require additional analysis prior to assigning a final activity label. In instances where the processor assigns more than one preliminary activity label, with each preliminary activity label having a confidence indicator within a predefined margin of each other, the processor may then determine to perform additional analysis. In such a configuration, the processor may adjust the predefined margin over time.

In other configurations, the processor may determine to perform additional analysis when the preliminary activity label is a commonly confused preliminary activity. Examples of commonly confused activities may be slow moving, low energy activities such as sitting compared to driving or fast moving, high energy activities like running compared against bicycling. In other instances, the current device status may be a factor for determining whether to perform additional analysis. For example, if the activity recognition device has a "low battery" state, this factor may weigh in favor of performing additional analysis prior to assigning a final activity label to a time window. Additionally, a low battery status may be a condition for the current device to send data to an exterior or external processor for additional processing prior to determining a final activity label.

If the processor determines that no additional analysis should be performed, the activity recognition device assigns a final activity label to the time window as shown in step 26. However, if the processor determines that additional analysis should be performed, the activity recognition proceeds to step 25 to perform additional analysis.

In step 25, where the processor determines that additional analysis should be performed, the analysis may be performed locally on the activity recognition device by the processor, or may be performed remotely by an external processor, such as some type of central monitoring system including, but not limited, computation in a cloud environment. Additional analysis may include computational escalation—performing more complex or resource intensive computations than were performed for the purpose of determining a preliminary activity label. Additional analysis may include at least one of the following algorithm techniques: neural networks, Bayesian analysis, random forest, support vector machine, and multi-level decision tree.

In step 26, the processor assigns a final activity label to the time window. In some instances, the processor will not have performed additional analysis and the final activity label will be the same as the preliminary activity label. In other instances, the processor may assign the final activity label to the time window based on the preliminary activity label for the time window and at least one final activity label for at least one prior time window. In some instances, the activity recognition device may transmit an alarm signal to a central monitoring system upon determination of a particular final activity label. For example, in the case where the activity recognition device is an electronic monitoring device, the activity recognition device may transmit an alarm if the final activity label is driving, but the location module is unable to detect any current location information.

Figure 3:
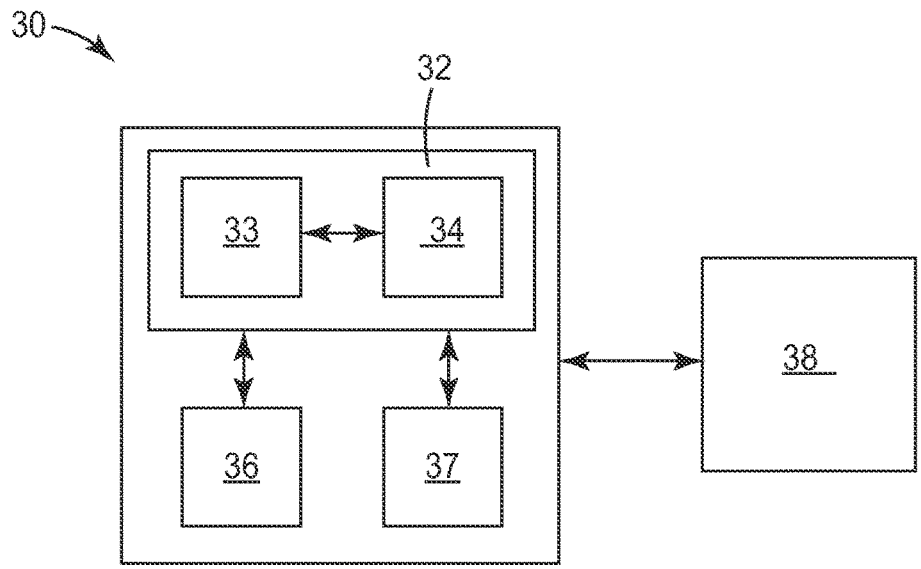
FIG. 3 is a block diagram of an activity recognition device and a remote processor.

FIG. 3 is a block diagram of an activity recognition device 30 and a remote processor 38. Activity recognition device 30 includes a processing unit 32 including both a processor 33 and movement sensor 34. Processor 33 may be any type of processor or microprocessor commonly used to process information or to control a variety of other electronic components. Processor 33 interacts with movement sensor 34 to receive data from movement sensor 34, such as a signal related to the movement of the person wearing activity recognition device 30. Movement sensor 34 can be configured to measure such a signal during a time window as defined by processor 33.

An exemplary time window may be in the range of 2 (two) seconds to 10 (ten) seconds and may contain a number of samples in the range of 8 (eight) to 1024 samples, as an example, not as a limitation. Movement sensor 34 may also be configured to operate in a very low power mode where sampling takes place occasionally over a longer time period, for example, once every five minutes, when the individual is sleeping or doing some other sedentary and longer-term activity. In general, data collection by the movement sensor 34 could range between 0.2 Hz and 50 Hz in frequency, but is not limited to previously defined range. The data collection frequency may be dependent upon the type of activity being detected. For example, faster moving activities, such as running, may require a higher sample rate (closer to 50 Hz) than slower moving activities such as sleeping. The size of a time window may also be related to data collection rate. A time window should have enough samples for processor 33 to assign a preliminary activity level with a reasonable confidence level.

Processor 33 may compute at least one numerical descriptor from the measured signal and assign at least one preliminary activity label to the time window based on the numerical descriptor. The processor 33 may then determine whether to perform additional analysis dependent upon at least the preliminary activity label; and then the processor assigns a final activity label to the time window.

In another configuration, the processor 33 may assign at least one preliminary activity label and confidence indicator to the time window based on at least one numerical descriptor computed from the measured signal. The processor 33 may then determine whether to perform additional analysis dependent upon at least the confidence indicator and the processor then assigns a final activity label to the time window.

Processing unit 32 may further include a location unit 37. A location unit 37 may be any device that provides an estimated geographical location for activity recognition device 30. Examples of a location unit 37 include the following technologies: GPS, Cellular Triangulation, WIFI triangulation and GNSS. In some configurations, processor 33 may be configured to estimate a location of the person using at least both of the signal from the movement sensor and data from the location module.

Activity recognition device 30 may also include a communications unit 36 to allow activity recognition device 30 to communicate with external devices. For example, when processor 33 determines that computational escalation is required, processor 33 may transmit the required data to external processor 38 to complete the additional processing prior to assigning a final activity label to a given time window.

While not shown in FIG. 3, activity recognition device 30 may further include an emergency notification component. Emergency notification component may be triggered manually, such as by a button or switch, or may be triggered automatically upon the detection of certain criteria, such as no movement of the person wearing activity recognition device 30 for a defined period of time. When emergency notification component is triggered, communication unit 36 may transmit information to an external device such as external processor 38, a central monitoring system, an emergency alert system, or other location. The information transmitted may include the location of the activity recognition device 30, the time the emergency notification is transmitted, and the reason that the emergency notification is transmitted.

Figure 4:
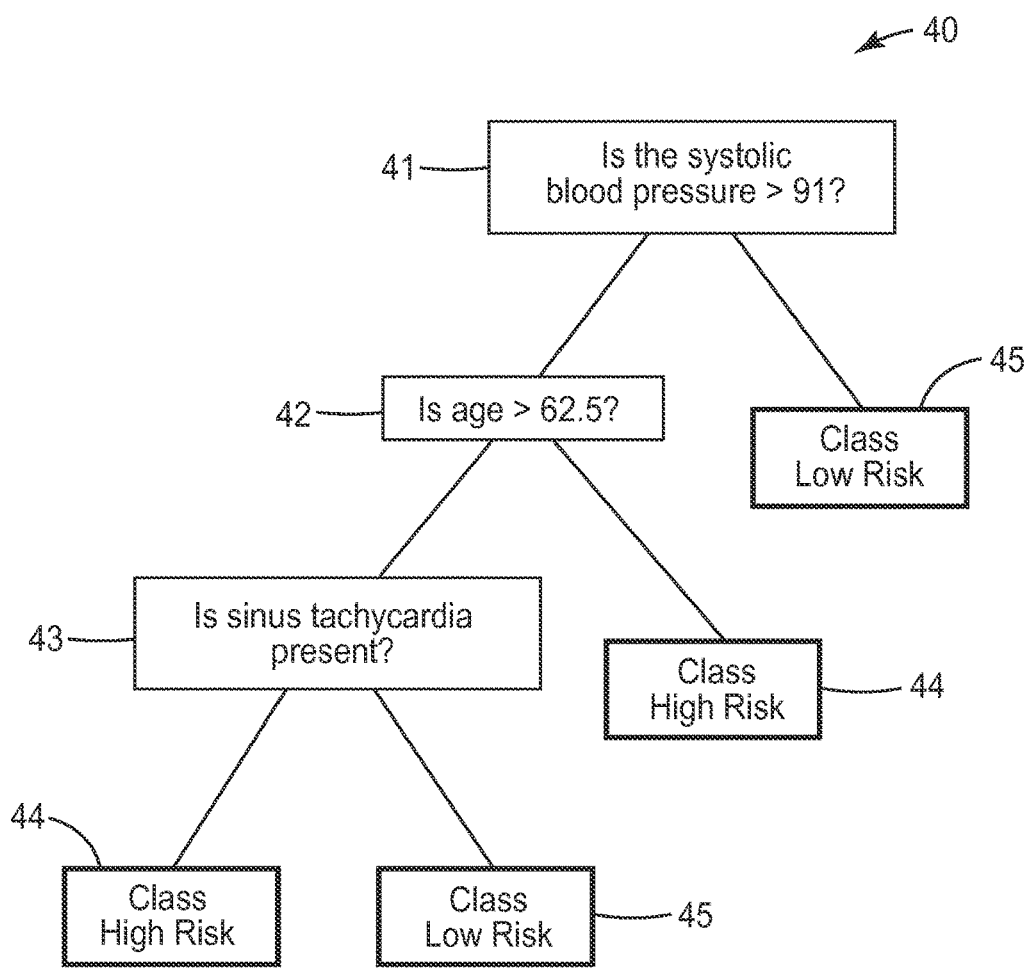
FIG. 4 shows an exemplary decision tree for assigning a preliminary activity label to a time window.

FIG. 4 shows an exemplary decision tree 40 such as one that may be used for assigning a preliminary activity label to a time window. Decision tree 40 uses a series of one or more factors 41, 42, 43 to reach an outcome—such as a high risk 44 or low risk 45 classification for risk of heart attack patients after their initial 24 hours of monitoring. While decision tree 40 uses factors related to a person's age and health to determine a risk profile, a decision tree based on similar principles may be used to determine a preliminary activity label for a time window. Factors used in a decision tree for determining a preliminary activity label may be based on, for example, the value of the numerical descriptor (s) assigned to the time window, the confidence indicator associated with the numerical descriptors, the numerical descriptor for one or more previous time windows, location information, environment information, device state and risk level or other characterizing information for the individual wearing the device. Outcomes associated with a decision tree may be any type of preliminary activity label, such as walking, driving, sleeping, sitting, running, eating, and bicycling. Other factors and outcomes will be apparent to one of skill of the art implementing this invention upon reading the present disclosure. Further, a decision tree is simply one of multiple techniques that may be used to assign a preliminary activity label to a particular time window. Other techniques used to assign a preliminary label to a time window will be apparent to one of skill in the art upon reading the present disclosure and are intended to be included in the scope of the present disclosure.

Figure 5:
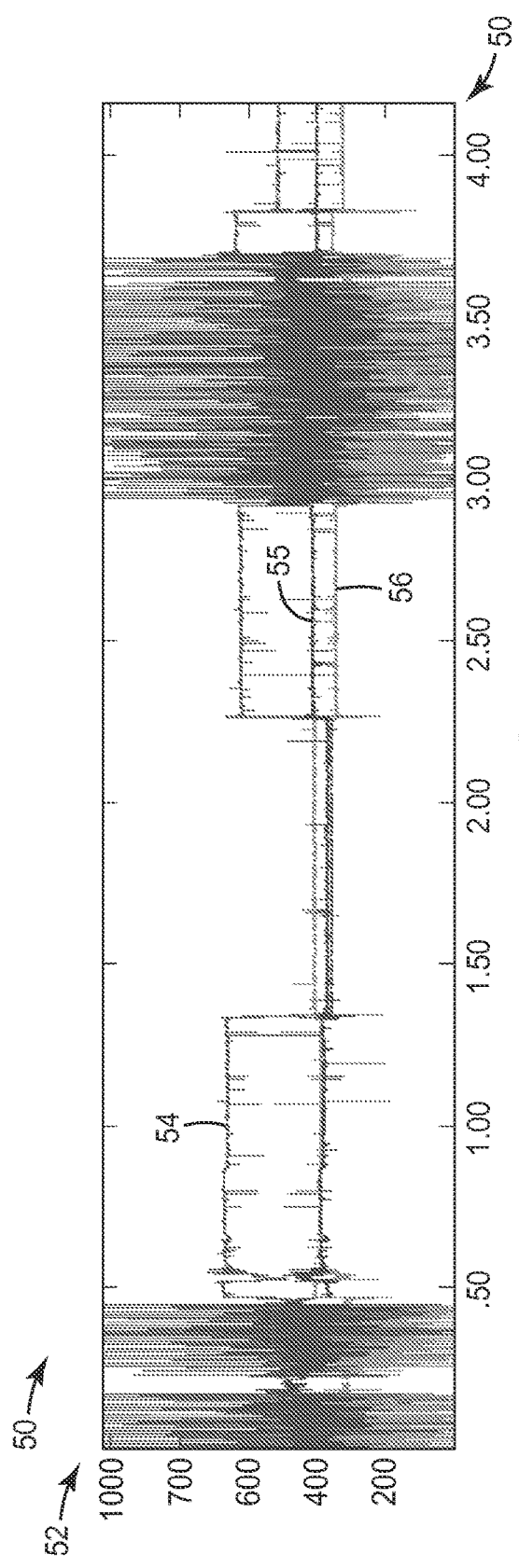
FIG. 5 shows exemplary data from a movement sensor over multiple time windows.

FIG. 5 is an accelerometer data graph 50 showing exemplary data an activity recognition device worn by an individual over a period of approximately 384 seconds. Graph 50 shows the magnitude of three axes 54, 55 and 56 of movement as measured by an accelerometer, across a time axis 51. Data axis 54, 55, 56 includes both a static component (driven by gravity) and a dynamic component. The sample rate for this particular graph was 20 Hz, the sampling period extends over 384 seconds.

Figure 6:
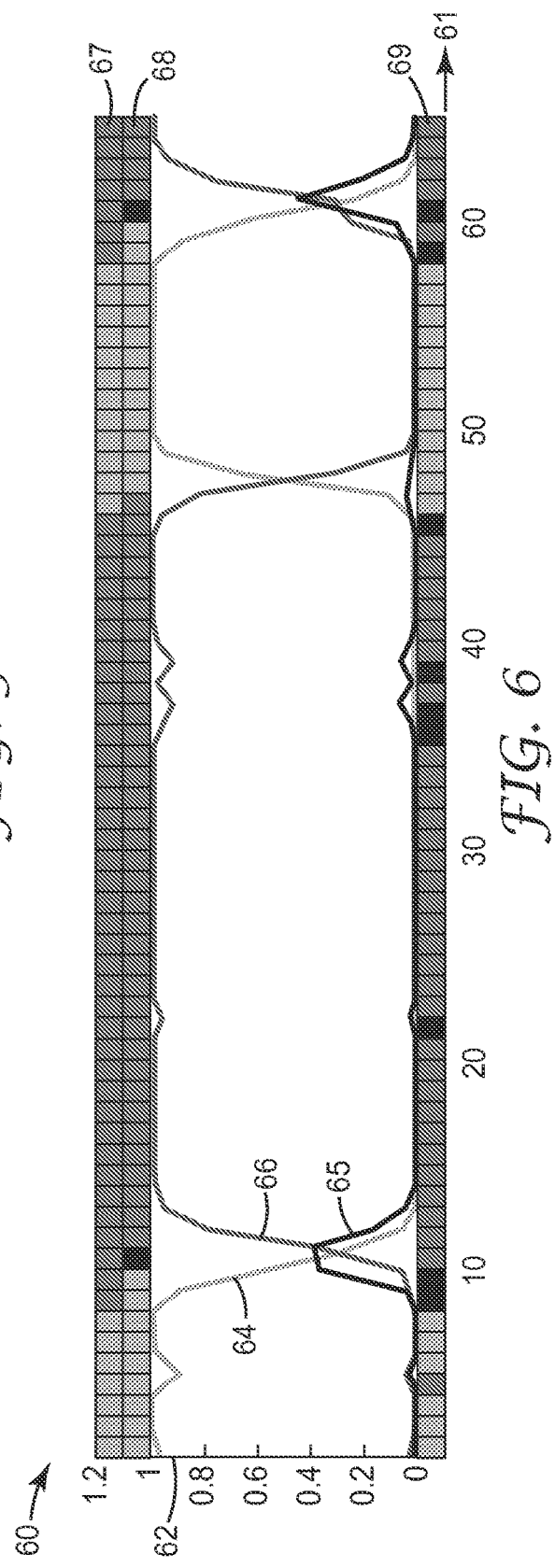
FIG. 6 shows exemplary numerical descriptors associated with the movement data from FIG. 5 over multiple time windows.

FIG. 6 shows graph 60 illustrating belief values for activity labels associated with the movement data from FIG. 5 over multiple time windows. The horizontal axis 61 shows time over 6-second time windows. As discussed throughout, shorter or longer time windows could be used consistent with the present disclosure. The vertical axis 62 shows belief values related to each of the activities, walking 64, driving 65 or resting 66, during a given time window. Belief values can be associated with a likelihood that a given activity is being performed during a given time window. Belief values differ from confidence indicators in that the sum of all belief values for all activities for a particular time window is 1.0.

The top layer of activity labels indicates the actual activity labels 67 for the activity being performed by the person wearing the activity monitoring device as recorded by that individual. During approximately the first seven time windows, the individual was walking. During time windows 8-45, the individual was resting. From time windows 45 to 57, the individual was walking again. And during time windows 58-64, the individual was resting.

The bottom layer of activity labels indicates preliminary activity labels 69 for each time window based on the accelerometer data associated with that time window as shown in FIG. 5. There are more frequent transitions between activities as shown in the preliminary activity labels 69 than when compared to actual activity labels 67.

Final activity labels 68, shown directly below actual activity labels 67 show changes made to the preliminary activity labels 69 after additional analysis. The additional analysis was based in part on the confidence indicator for the assigned activity during a given time window. As can be seen, the final activity labels 68 have a high degree of accuracy when compared with actual activity labels 67.

Confidence indicators for walking 64, driving 65 and resting 66 are not shown in FIG. 6. However, a confidence indicator for the preliminary activity label for each time window could be calculated the belief values.

For example, in FIG. 6 the belief value for each activity is represented by the lines 64, 65, 66. As the actual activity label 67 changes, the associated belief values change. A confidence indicator for the preliminary activity label 69 could be derived by looking at how close the belief values are to one another. For example, during time window 11, all three belief values are close to one another, i.e. all roughly around 0.33. During this time window, a calculated confidence indicator would be very low because the belief values indicate that all activities have an equal chance of being the actual activity of the user. In this case, the device may send data related to time window 11 to a remote processor for escalated or additional processing.

The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

EXAMPLES

While the examples represent specific scenarios and methods in which the activity recognition process interacts with individuals and devices, permutations and variations on these examples will be apparent to one of skill in the art upon reading the present disclosure. The various methods and devices shown in and discussed in the context of each of the examples can be adapted to meet other particular use cases and work flows. Further, methods and devices shown in the examples may be combined in variety of ways; the examples are only intended to illustrate a sampling of the possible processes made possible by the present disclosure. Finally, as technology evolves some of the methods or devices in the examples may become unnecessary or obsolete; however, the scope of the inventive concepts disclosed and claimed herein will still be understood by those of skill in the art.

Example 1

Activity Recognition Process Activation

A device used to recognize activity is required to be of a small form factor and lightweight to minimize interference with the regular motion and movement of a person that it is attached. Size and weight constraints therefore require efficient management of device housing space for providing energy to the device (e.g., battery) and for data storage. In an escalating trend, electronic monitoring (EM) devices or bracelets are being attached to offenders as a method to track their location to maintain the conditions of a sentence or parole. These EM devices are outfitted with global positioning system (GPS), or other location systems, to provide and communicate location and corresponding date/time stamps of an offender. In certain circumstances, GPS communication of the EM device may be interrupted, blocked, or disabled. When GPS communication is disrupted, the activity recognition process is activated to actively monitor the actions of an offender until GPS communication is restored.

There is a trade-off between the energy necessary to power an EM device and data processing capabilities. Simultaneous activation of both GPS and the activity recognition process may be redundant and lead to reduced performance of the EM device (e.g., rapid loss of power or extensive use of processor memory). However, both may be active in situational circumstances. As an example, an offender has an EM device attached to their ankle. GPS communication broadcasts their current location as their place of residence. An hour later, GPS still registers their place of residence as their current location, but suddenly the GPS signal is lost. The activity recognition process is immediately activated and records that an offender transitioned from a resting position and then walked for twenty minutes. The activity recognition process continues, monitoring motion and movement, until GPS communication is restored and/or an alert is generated.

Example 2

Activity Recognition Process Alert Generation

Alerts or alarms are generated and transmitted, from a device, when activity transitions or durations are abrupt or constant for prolonged periods of time. Alerts or alarms are notifications sent to personnel assigned to monitor a person with an attached device. As an example, an offender has an EM device attached to their ankle. GPS communication and the activity recognition process are active. The activity recognition process records that an offender was cycling for sixty minutes and then driving for ten minutes. GPS communicates that the offender was at their place of residence for the last seventy minutes. An alert is generated as the cycling activity duration was unchanging and the driving activity was abrupt at a location where it normally would not occur.

Variations on the disclosure described above will be apparent to one of skill in the art upon reading the present disclosure, and are intended to be included within the scope of the present disclosure. A wide range of activities may be detected in addition to those discussed explicitly herein, and are within the scope of the present disclosure. Further, a variety of analysis methods may be used consistent with the disclosed analysis steps and processes.

What is claimed is:

1. A computing device comprising:
a physical housing configured to be worn by a user;
at least one movement sensor enclosed within the physical housing;
at least one computer processor enclosed within the physical housing;
at least one memory enclosed within the physical housing, wherein the memory comprises instructions that, when executed by the at least one computer processor, cause the at least one computer processor to:
in response to receiving from the movement sensor, a set of movement data based on one or more signals that correspond to movement of the user during a time window, generate at least one numerical descriptor for the time window;
generate, based at least in part on the at least one numerical descriptor for the time window, a confidence indicator that corresponds to a preliminary activity label, wherein the preliminary activity label is indicative of movement of the user during the time window;
in response to determining that the confidence indicator corresponding to the preliminary activity label fails to satisfy a condition, initiate a set of operations to determine a final activity label for the time window that are at least more computationally complex than a set of operations used to determine the preliminary activity label, wherein the final activity label is indicative of movement of the user during the time window; and in response to determining that the final activity label satisfies at least one criterion, generating a notification based at least in part on the final activity label.

2. The computing device of claim 1, wherein the at one least movement sensor is included in a plurality of sensors, wherein the memory comprises instructions that, when executed by the at least one computer processor, cause the at least one computer processor to:

in response to receiving from each respective sensor in the plurality of sensors, a respective set of sensor data based on one or more signals generated by the respective sensor during a time window, generate the at least one numerical descriptor for the time window.

3. The computing device of claim 1, wherein the memory comprises instructions that, when executed by the at least one computer processor, cause the at least one computer processor to:

generate a plurality of numerical descriptors for the time window that includes the at least one numerical descriptor for the time window.

4. The computing device of claim 1, wherein the memory comprises instructions that, when executed by the at least one computer processor, cause the at least one computer processor to:

generate a plurality of preliminary activity labels for the time window that includes the preliminary activity label;

generate, for each respective preliminary activity label of the plurality of preliminary activity labels and based at least in part on one or more one numerical descriptors for the time window, a respective confidence indicator that corresponds to the respective preliminary activity label;

select a set of preliminary activity labels from the plurality of activity labels based at least in part on the respective confidence indicators that correspond to the set of preliminary activity labels; and wherein determination of the final activity label for the time window is based at least in part on one or more of the set of preliminary activity labels.

5. The computing device of claim 1, wherein to determine that the confidence indicator corresponding to the preliminary activity label fails to satisfy the condition, the memory comprises instructions that, when executed by the at least one computer processor, cause the at least one computer processor to:

determine that the confidence indicator is less than a predefined threshold.

6. The computing device of claim 1, wherein the preliminary activity label is a first preliminary activity label, wherein to determine that the confidence indicator corresponding to the preliminary activity label fails to satisfy the condition, the memory comprises instructions that, when executed by the at least one computer processor, cause the at least one computer processor to:

determine that the first preliminary activity label corresponds to at least one of a speed of movement or magnitude of energy that is less than the condition.

7. The computing device of claim 1, wherein to initiate the set of operations to determine the final activity label for the time window, the memory comprises instructions that, when executed by the at least one computer processor, cause the at least one computer processor to:

send, to a remote computing device that performs at least a portion of the set of operations that are at least more computationally complex than the set of operations used to determine the preliminary activity label, data related to the time window that was generated by the computing device; and receive, from the remote computing device data usable to determine the final activity label.

8. The computing device of claim 1, wherein the memory comprises instructions that, when executed by the at least one computer processor, cause the at least one computer processor to perform the set of operations to determine the final activity label for the time window that are at least more computationally complex using at least one of a neural network, Bayesian analysis, random forest, support vector machine, or decision tree.

9. The computing device of claim 1, wherein the time window is a first time window, the final activity label indicative of movement of the user during the first time window is based at least in part on the preliminary activity label for the first time window and the final activity label for a second time window that precedes the first time window.

10. The computing device of claim 1, wherein to generate the notification, the memory comprises instructions that, when executed by the at least one computer processor, cause the at least one computer processor to:

in response to determining that the final activity label corresponds to a particular final activity label, send an alarm to a remote computing device.

11. The computing device of claim 10, wherein to generate the notification, the memory comprises instructions that, when executed by the at least one computer processor, cause the at least one computer processor to:

send the alarm to the remote computing device based on determining that the final activity label corresponds to the particular final activity label and that a location sensor cannot detect location information.

12. The computing device of claim 1, wherein to generate the notification, the memory comprises instructions that, when executed by the at least one computer processor, cause the at least one computer processor to:

send, to a remote computing device, information comprising one or more of a location of the computing device, time information, or a reason for sending the information.

13. The computing device of claim 1, wherein to generate the confidence indicator that corresponds to the preliminary activity label, the memory comprises instructions that, when executed by the at least one computer processor, cause the at least one computer processor to:

generate the confidence indicator that corresponds to the preliminary activity label based at least in part on at least one of age or health of the user.

14. The computing device of claim 1, wherein to generate the confidence indicator that corresponds to the preliminary activity label, the memory comprises instructions that, when executed by the at least one computer processor, cause the at least one computer processor to:

generate the confidence indicator that corresponds to the preliminary activity label based at least in part on at least one of location of the computing device, information corresponding to the environment that includes the computing device, a risk level for the user wearing the device, or information that characterizes the user wearing the device.

15. The computing device of claim 1, wherein the memory comprises instructions that, when executed by the at least one computer processor, cause the at least one computer processor to:
generate at least two respective belief values that correspond to at least two respective activities;
determine a magnitude of closeness between the at least two respective belief values; and
generate the confidence indicator that corresponds to the preliminary activity label based at least in part on the magnitude of closeness between the at least two respective belief values.

16. A non-transitory computer-readable storage medium comprising instructions that, when executed by one or more computer processors, cause the one or more computer processors to:
in response to receiving from a movement sensor, a set of movement data based on one or more signals that correspond to movement of a user during a time window, generate at least one numerical descriptor for the time window;
generate, based at least in part on the at least one numerical descriptor for the time window, a confidence indicator that corresponds to a preliminary activity label, wherein the preliminary activity label is indicative of movement of the user during the time window;
in response to determining that the confidence indicator corresponding to the preliminary activity label fails to satisfy a condition, initiate a set of operations to determine a final activity label for the time window that are at least more computationally complex than a set of operations used to determine the preliminary activity label, wherein the final activity label is indicative of movement of the user during the time window; and
in response to determining that the final activity label satisfies at least one criterion, generating a notification based at least in part on the final activity label.

17. The non-transitory computer-readable storage medium of claim 16, wherein the movement sensor is included in a plurality of sensors, and further comprising instructions that, when executed by the one or more computer processors, cause the one or more computer processors to:
in response to receiving from each respective sensor in the plurality of sensors, a respective set of sensor data based on one or more signals generated by the respective sensor during a time window, generate the at least one numerical descriptor for the time window.

18. The non-transitory computer-readable storage medium of claim 16, further comprising instructions that, when executed by one or more computer processors, cause the one or more computer processors to:
generate a plurality of numerical descriptors for the time window that includes the at least one numerical descriptor for the time window.

19. The non-transitory computer-readable storage medium of claim 16, further comprising instructions that, when executed by the one or more computer processors, cause the one or more computer processors to:
generate a plurality of preliminary activity labels for the time window that includes the preliminary activity label;
generate, for each respective preliminary activity label of the plurality of preliminary activity labels and based at least in part on one or more numerical descriptors for the time window, a respective confidence indicator that corresponds to the respective preliminary activity label;
select a set of preliminary activity labels from the plurality of activity labels based at least in part on the respective confidence indicators that correspond to the set of preliminary activity labels; and
wherein determination of the final activity label for the time window is based at least in part on one or more of the set of preliminary activity labels.

20. The non-transitory computer-readable storage medium of claim 16, wherein to determine that the confidence indicator corresponding to the preliminary activity label fails to satisfy the condition, comprises instructions that, when executed by the at least one computer processor, cause the at least one computer processor to:
determine that the confidence indicator is less than a predefined threshold.

* * * * *